(12) United States Patent
Sheng et al.

(10) Patent No.: US 12,115,274 B2
(45) Date of Patent: Oct. 15, 2024

(54) POROUS TRICALCIUM PHOSPHATE MATERIAL, METHOD FOR BONE HEALING USING THE SAME, AND MANUFACTURING METHOD THEREOF

(71) Applicant: Popeye Marine Biotechnology Limited, New Taipei (TW)

(72) Inventors: Yi-Jen Sheng, New Taipei (TW); Yu-Hao Chan, New Taipei (TW); Yu-Quan Peng, New Taipei (TW)

(73) Assignee: POPEYE MARINE BIOTECHNOLOGY LIMITED, New Taipei (TW)

( * ) Notice: Subject to any disclaimer, the term of this patent is extended or adjusted under 35 U.S.C. 154(b) by 52 days.

(21) Appl. No.: 17/692,460

(22) Filed: Mar. 11, 2022

(65) Prior Publication Data
US 2023/0149597 A1    May 18, 2023

(30) Foreign Application Priority Data
Nov. 12, 2021 (TW) ................... 110142116

(51) Int. Cl.
  *A61L 27/12* (2006.01)
  *A61L 27/56* (2006.01)

(52) U.S. Cl.
  CPC .............. *A61L 27/12* (2013.01); *A61L 27/56* (2013.01); *A61L 2430/02* (2013.01)

(58) Field of Classification Search
None
See application file for complete search history.

(56) References Cited

U.S. PATENT DOCUMENTS

| | | | |
|---|---|---|---|
| 4,717,556 A | 1/1988 | Kawamura | |
| 4,861,733 A * | 8/1989 | White | A61L 27/56 623/23.61 |
| 8,936,638 B2 | 1/2015 | Schwartz | |
| 2007/0178220 A1 | 8/2007 | Karlinsey | |
| 2010/0094419 A1 | 4/2010 | Kim | |

FOREIGN PATENT DOCUMENTS

| | | |
|---|---|---|
| CN | 1644221 A | 7/2005 |
| CN | 100366301 C | 2/2008 |
| CN | 102091348 A | 6/2011 |
| RU | 2472516 C1 * | 1/2013 |

OTHER PUBLICATIONS

Bone Jin China and foreign countries, How to choose a bone graft, 20210212, web article.
Pek Karacan et al., The natural nano-bioceramic powder production from organ pipe red coral (*Tubipora musica*) by a simple chemical conversion method, 20171107, Journal of the Australian Ceramic Society.
Yang Shunqing et al., Inorganic biomaterials, 200810, China.
Joshua Chou et al., Bone regeneration of calvarial defect using marine calcareous-derived beta-tricalcium phosphate macrospheres, 2014, Journal of Tissue Engineering.
A. V. Nesterova et al., Cytocompatibility and Matrix Properties of Surfaces of Nanostructured Calcium Phosphate Cements, 2019, Inorganic Materials: Applied Research.
Marc Bohner et al., β-tricalcium phosphate for bone substitution: Synthesis and properties, 2020, Acta Biomaterialia.
Ingo Sethmann et al., Development of Phosphatized Calcium Carbonate Biominerals as Bioactive Bone Graft Substitute Materials, Part I: Incorporation of Magnesium and Strontium Ions, 20181202, Journal of Functional Biomaterials.

* cited by examiner

*Primary Examiner* — David J Blanchard
*Assistant Examiner* — Daniel F Coughlin
(74) *Attorney, Agent, or Firm* — WPAT, P.C

(57) ABSTRACT

The present invention provides a porous tricalcium phosphate material, modified from a coral bone and having a plurality of pores, wherein the average compressive strength of the porous tricalcium phosphate material is 4 kgf to 9 kgf. Besides, the present invention also provides a method for bone healing and a manufacturing method for the porous tricalcium phosphate material. The porous tricalcium phosphate material of the present invention has the advantages of biocompatibility and no immunological rejection response, and also has significantly better mechanical properties and bone healing efficacy so as to better meet the needs of the patients.

7 Claims, 6 Drawing Sheets

POROUS TRICALCIUM PHOSPHATE MATERIAL, METHOD FOR BONE HEALING USING THE SAME, AND MANUFACTURING METHOD THEREOF

CROSS-REFERENCE TO RELATED APPLICATION

Pursuant to 35 U.S.C. § 119(a), this application claims the benefits of the priority to Taiwan Patent Application No. 110142116, filed on Nov. 12, 2021, which is incorporated by reference herein by its entirety.

BACKGROUND OF THE INVENTION

1. Field of the Invention

The present invention relates to a porous tricalcium phosphate material, especially a medical porous tricalcium phosphate material, a method for bone healing using the same, and a manufacturing method thereof.

2. Description of the Prior Arts

The growth rate of human bones is slow. When the bone is damaged, a bone grafting medical device is generally required for bone healing. The common types of bone grafting medical device comprise: (1) autologous bones, which are taken from the patient himself/herself, and will not result in immunological rejection. However, additional surgery is required, and the quantity of bones and bone type options are limited; (2) demineralized bones, which are the human bones taken from body bequest and further treatment is required before allotransplantation. The quantity of bones and bone type options are limited as well; (3) sintered biological bones, which are xenogeneic bone substitutes, have the structure similar to that of human bones, but accompanied with the risk of immunological rejection response; and (4) synthetic artificial bones and bone cements: The quantity of bones and bone type options thereof are not limited, and they are currently the most common type of the bone grafting medical device.

Synthetic artificial bones and bone cements have the advantages of availability, convenience, easy storage and no risk of disease transmission, which warrants a wide application in medical practices, so there is a necessity to develop a novel bone grafting medical device which can be mass-produced.

SUMMARY OF THE INVENTION

To provide a better bone grafting medical device, the present invention provides a porous tricalcium phosphate material, modified from a coral bone and having a plurality of pores, wherein the average maximum load of the porous tricalcium phosphate material is 4 kilogram-force (kgf) to 9 kgf.

The ingredient of coral bones is calcium carbonate. According to the present invention, the adoption of coral bones to substitute general calcium carbonate material for modification will result in that the bone grafting medical device of the present invention has a significantly higher average compressive strength in comparison with the tricalcium phosphate of the commercial bone grafting medical device. As the patients need to carry out daily activities during the bone healing period, the bones must support the body weight. Therefore, the porous tricalcium phosphate material with higher average compressive strength could lower the risk of bone material degradation accelerated due to the stress from the body weight of the patients, and is more suitable for bone healing. Besides, the present invention also has dental applications, such as filling or rebuilding the alveolar bone of the mandible after tooth extraction or bone cutting. As the present invention is biocompatible and absorbable for the human body, it temporarily fills the space reserved for the new bone during the recovery period of gradual new bone formation, which not only enhances the healing efficacy, but also improves the alveolar bone's tolerance towards the occlusal force during the recovery period so as to maintain the normal structure and function of the recovery site.

The compressive strength of the present invention also means the maximum load that the porous tricalcium phosphate material can bear prior to failure, divided by its cross sectional area.

The term "modified from a coral bone" means that the coral bone serves as a raw material of calcium carbonate, and is added with dicalcium phosphate for reaction to obtain tricalcium phosphate. Preferably, the tricalcium phosphate of the present invention is obtained firstly by mixing a coral calcium carbonate, dicalcium phosphate and water to obtain a first mixture, drying the first mixture at 50° C. to 60° C. for 7 hours to 10 hours to obtain a second mixture, and then heating the second mixture at 500° C. to 600° C. for 2 hours to 3 hours and further heating at 1000° C. to 1100° C. for 2 hours to 4 hours.

The "average maximum load" of the porous tricalcium phosphate material may be 4 kgf, 4.5 kgf, 5 kgf, 5.5 kgf, 6 kgf, 6.5 kgf, 7 kgf, 7.5 kgf, 8 kgf, 8.5 kgf or 9 kgf, for example. Preferably, the average maximum load of the porous tricalcium phosphate material is 5 kgf to 7 kgf. More preferably, the average maximum load of the porous tricalcium phosphate material is 5.8 kgf to 6.6 kgf. In one embodiment, the "average maximum load" is the average maximum load of the porous tricalcium phosphate material obtained in the form of a compressed tablet. More preferably, the "average maximum load" is the average compressive strength obtained according to the regulations of ISO 13175-3(2012). Further preferably, the "average maximum load" is the average compressive strength obtained according to the Charter of 4.6.2.4 in the regulations of ISO 13175-3(2012).

In one embodiment, the aforementioned compressed tablet has a thickness of 5 mm and a diameter of 13 mm. Preferably, the compressed tablet is prepared from the porous tricalcium phosphate material with the average diameters from 0.1 millimeters (mm) to 5 mm, for example, 0.1 mm, 0.25 mm, 0.5 mm, 1 mm, 1.5 mm, 2 mm, 2.5 mm, 3 mm, 3.5 mm, 4 mm, 4.5mm or 5 mm by hydraulic pressure. More preferably, the compressed tablet is tested at the test speed of 0.5 mm/min.

Tricalcium phosphate is the major ingredient of human bones and can be used for bone healing. Preferably, the porous tricalcium phosphate material of the present invention is pure tricalcium phosphate. The pure tricalcium phosphate of the present invention means it substantially consists of tricalcium phosphate. The formula of the pure tricalcium phosphate of the present invention is $Ca_3(PO_4)_2$.

In one embodiment, the porous tricalcium phosphate material comprises a plurality of tricalcium phosphate particles and is in a state of powders. In another embodiment, the porous tricalcium phosphate material may be prepared in the form of a colloidal suspension to facilitate the usage. Preferably, the particle diameter of the porous tricalcium phosphate material is 0.1 mm to 5 mm, for example, 0.1 mm, 0.2 mm, 0.25 mm, 0.5 mm, 1 mm, 2 mm, 3 mm, 4 mm or 5 mm. More preferably, the particle diameter of the porous tricalcium phosphate material is 0.25 mm to 0.5 mm, 0.5 mm to 1.0 mm, 1.0 mm to 2.0 mm or 2.0 mm to 3.0 mm.

Preferably, the porous tricalcium phosphate material is β-tricalcium phosphate (β-TCP). More preferably, the porous tricalcium phosphate material is pure β-tricalcium phosphate.

Preferably, the weight ratio of calcium to phosphorus of the porous tricalcium phosphate material is 1.5 to 1.6. More preferably, the weight ratio of calcium to phosphorus of the porous tricalcium phosphate material is 1.54 to 1.56.

The present invention has a plurality of pores and is similar to human bones, which is beneficial for bone cell adhesion and proliferation, and facilitates the bone cells growing towards the inside of the porous tricalcium phosphate material of the present invention, for example, the pores, or towards the inside of the stack of the porous tricalcium phosphate material, for example, the porous tricalcium phosphate material is in the form of particles, so the bone cells grow along with the surface of the particles and towards the center of the stack. Preferably, the average total pore volume of the porous tricalcium phosphate material is 0.35 mL/g to 0.51 mL/g. More preferably, the average total pore volume thereof is 0.4 mL/g to 0.46 mL/g. Further preferably, the average total pore volume thereof is 0.425 mL/g to 0.445 mL/g.

Preferably, the average pore size of the porous tricalcium phosphate material is 1.3 µm to 1.4 µm. More preferably, the average pore size of the porous tricalcium phosphate material is 1.33 µm to 1.37 µm.

In one embodiment, the average total porosity of the porous tricalcium phosphate material is calculated by $\varepsilon p = Vt \, \rho s / (Vt \, \rho s + 1) \times 100\%$, wherein $\varepsilon p$ is total porosity, $Vt$ is total pore volume, and $\rho s$ is density. The units for $\varepsilon p$, $Vt$ and $\rho s$ are %, mL/g and g/mL, respectively.

Preferably, the average total porosity of the porous tricalcium phosphate material is 43% to 47%. More preferably, the average total porosity of the porous tricalcium phosphate material is 44.5% to 45.5%. The denominator of the total porosity is volume, which is different from that of the total pore volume, which is weight.

Preferably, the density of the porous tricalcium phosphate material is 1.8 g/mL to 2 g/mL. More preferably, the density of the porous tricalcium phosphate material is 1.85 g/mL to 1.89 g/mL. General tricalcium phosphate has no pores and the density thereof is 3.14 g/mL. As the porous tricalcium phosphate material of the present invention has a lot of pores, the density thereof is significantly lower.

Preferably, the average total pore volume, the average pore size, the average total porosity and density are obtained according to the regulations of ISO 13175-3(2012). More preferably, the average total pore volume, the average pore size, the average total porosity and density are obtained according to the Charter of 4.4.2.1 in the regulations of ISO 13175-3(2012).

Preferably, the crystallinity of the porous tricalcium phosphate material is 79.4% to 81%, and the amorphous thereof is 19% to 20.6%. More preferably, the crystallinity of the porous tricalcium phosphate material is 80.2%, and the amorphous thereof is 19.8%. Therefore, the porous tricalcium phosphate material of the present invention has a high proportion of crystals.

Preferably, the crystallinity and the amorphous are obtained according to the regulations of ISO 13175-3(2012). More preferably, the crystallinity and the amorphous are obtained according to the Charter of 4.2 in the regulations of ISO 13175-3(2012).

As tricalcium phosphate is the major ingredient of human bones, the porous tricalcium phosphate material of the present invention has good biocompatibility so as to lower the risk of immunological rejection response, has extremely low water solubility and has biodegradability so that the slow degradation thereof in a long period can gradually provide a space for new bone formation to facilitate bone healing.

The porous tricalcium phosphate material of the present invention has an average elastic modulus that is significantly higher than that of the commercial product and reduces the cracking risk resulting from the application of force, and is more suitable for bone healing. Preferably, the average elastic modulus of the porous tricalcium phosphate material is 0.19 Gpa to 0.65 Gpa, for example, 0.19 Gpa, 0.22 Gpa, 0.25 Gpa, 0.28 Gpa, 0.31 Gpa, 0.34 Gpa, 0.37 Gpa, 0.40 Gpa, 0.43 Gpa, 0.46 Gpa, 0.49 Gpa, 0.51 Gpa, 0.54 Gpa, 0.57 Gpa, 0.60 Gpa, 0.63 Gpa or 0.65 Gpa. More preferably, the average elastic modulus thereof is 0.25 Gpa to 0.4 Gpa. Further preferably, the average elastic modulus thereof is 0.3 Gpa to 0.35 Gpa.

one embodiment, the "average elastic modulus" is the average elastic modulus obtained according to the regulations of ISO 13175-3(2012).

In one embodiment, the average elastic modulus is the average elastic modulus of the porous tricalcium phosphate material obtained in the form of a compressed tablet. Preferably, the compressed tablet for obtaining the value of the average elastic modulus is the same as that for obtaining the average compressive strength.

The coral bone of the present invention is obtained from the corals propagated by indoor farming, which is free of concerns for heavy metal contaminations. In one embodiment, lead, cadmium, mercury and arsenic are un-detected in the porous tricalcium phosphate material of the present invention.

Preferably, the corals are propagated by a coral farming method, comprising:
  providing a water tank, wherein the water tank contains seawater, and the seawater has calcium ions and magnesium ions;
  an inoculation step, comprising placing a coral on a base, and the base being placed in the water tank;
  a cultivating step, comprising maintaining the sea water to have a pH of 7.8 to 8.8, a salinity of 29 parts per thousand (ppt) to 37 ppt, an alkalinity of 7 dKH to 10 dKH, and a temperature of 20° C. to 26° C., a calcium ions concentration of 430 ppm to 500 ppm, and a magnesium ions concentration of 1290 ppm to 1500 ppm;
  a feeding step, comprising providing food to the coral;
  an illuminating step, comprising providing light to the coral for at least 6 hours a day; and
  a decontamination step, comprising removing a floating foam of the seawater and based on the total volume of the seawater in the water tank, filtering the seawater in an amount of at least 2.6 volume percent per minute.

In one embodiment, the frequency to monitor the seawater is 5 to 12 times a day. Preferably, the frequency to monitor the seawater is 8 to 12 times a day, such as 10 times a day.

In one embodiment, the frequency of the feeding step is 8 to 15 times a day. Preferably, the frequency of the feeding step is 1 to 3 times a week.

Preferably, the seawater further comprises phosphate, nitrite and nitrite, and the concentration of the phosphate is less than 0.03 ppm, the concentration of the nitrate is less than 0.5 ppm, and the concentration of the nitrite is less than 0.1 ppm.

Preferably, the food comprises rotifers or paramecium or a combination thereof.

Preferably, the coral comprises a small polyp stony coral.

More preferably, the small polyp stony coral is selected from the group consisting of *Acropora formosa*, *Acropora nobilis*, *Acropora austere*, *Acropora valenciennesi*, *Acropora pulchra*, *Acropora microphtha*, *Acropora intermedia* and *Acropora florida*.

The small polyp stony coral can secrete a large amount of calcium carbonate to form coral bones, and has high growing rate of the coral bones so as to lower the production cost. Besides, the ingredient of the coral bones is calcium carbonate, which is the same as that of the general calcium carbonate material. However, the porous tricalcium phosphate material, modified from the calcium carbonate of the coral bone raw materials, has significantly better average compressive strength and average elastic modulus in comparison with the general calcium carbonate material. Therefore, such advantages may result from the cause that the calcium carbonate powders obtained by grinding coral bones are different from the calcium carbonate raw material used in the commercial bone grafting medical device.

Preferably, the aforementioned coral farming method can further promote the growth rate of corals.

The present invention further provides a method for bone healing, comprising administering to a subject in need thereof a medical product, wherein the medical product comprises a porous tricalcium phosphate material, modified from a coral bone and having a plurality of pores, wherein the average maximum load of the porous tricalcium phosphate material is 4 kgf to 9 kgf; and the medical product is a drug or a medical device.

The bone healing comprises increasing the growth rate of new bones or increasing the space for bone cell adhesion. Preferably, the porous tricalcium phosphate material of the present invention is in the form of particles so as to further increase the surface area for bone cell adhesion.

The bone healing in the present invention also means the treatment of bone damage.

The porous tricalcium phosphate material in the method for bone healing of the present invention is the same as that disclosed in the claimed object of the present invention. According to the present invention, the porous tricalcium phosphate material of the present invention has significantly better bone healing efficacy in comparison with the tricalcium phosphate of the commercial bone grafting medical device.

Although the porous tricalcium phosphate material of the present invention and that of the commercial bone grafting medical device are tricalcium phosphate, the porous tricalcium phosphate material of the present invention has three advantages: significantly better average compressive strength, average elastic modulus and bone healing efficacy. Such advantages may result from the cause that the calcium carbonate powders obtained by grinding coral bones are different from the calcium carbonate raw material used in the commercial bone grafting medical device, and such cause further contributes to the difference of the mechanical and biochemical properties of the porous tricalcium phosphate material of the present invention after modification.

The present invention further provides a manufacturing method for the porous tricalcium phosphate material, comprising:
(1) grinding the coral bone into powders to obtain a coral calcium carbonate;
(2) mixing the coral calcium carbonate, dicalcium phosphate and water at a weight ratio of 0.8 to1.2:2.5 to 3.5:5.4 to 6.6 to obtain a first mixture;
(3) stifling the first mixture at a speed from 400 rpm to 500 rpm for 7 hours to 11 hours and then drying at 50° C. to 60° C. for 7 hours to 10 hours to obtain a second mixture; and
(4) heating the second mixture at 500° C. to 600° C. for 2 hours to 3 hours and then heating at 1000° C. to 1100° C. for 2 hours to 4 hours to obtain the porous tricalcium phosphate material.

In one embodiment, the porous tricalcium phosphate material in the manufacturing method of the present invention is the same as that disclosed in the claimed object of the present invention. The coral bone in the manufacturing method of the present invention is the same as that disclosed in the claimed object of the present invention.

To sum up, the porous tricalcium phosphate material of the present invention, serving as bioceramics, is significantly better than metal and plastic materials. Further, the porous tricalcium phosphate material of the present invention has significantly better mechanical properties of average compressive strength and average elastic modulus, biocompatibility, and better bone healing efficacy so as to better meet the medical needs of the patients and demonstrate great market potential.

DETAILED DESCRIPTION OF THE PREFERRED EMBODIMENTS

Figure 1:
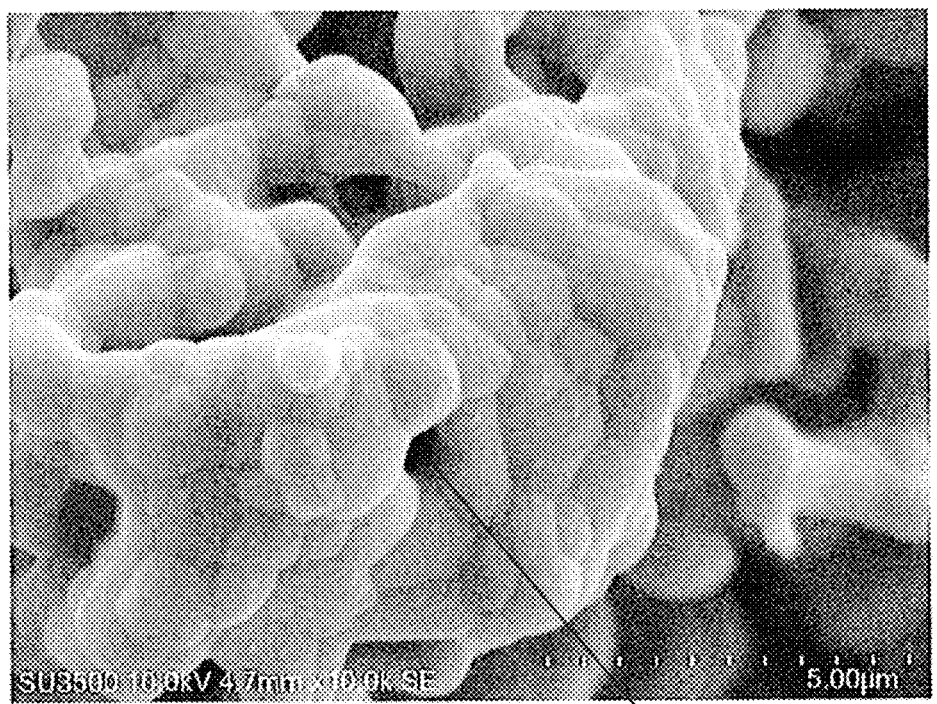
FIG. 1 is the magnified photo of the porous tricalcium phosphate material of Example 1 of the present invention.

The present invention is further explained through the following embodiments. A person having ordinary skill in the art can easily understand the advantages and efficacies achieved by the present invention. The present invention should not be limited to the contents of the embodiments. A person having ordinary skill in the art can make some improvement or modifications which are not departing from the spirit and scope of the present invention to practice or apply the content of the present invention.

PREPARATION EXAMPLE 1

Coral Bone

The coral was propagated in a glass culturing tank within a building in a closed system with circulating seawater, which means that the glass culturing tank did not communicate with the open sea to directly draw or discharge seawater. The seawater of the present invention was obtained from natural sea, which required sedimentation and purification first, and then the parameters of the seawater as described later were adjusted within the predetermined range. The coral comprised *Acropora Formosa, Acropora nobilis* and *Acropora austere,* each of which was propagated in separate glass culturing tanks. All the coral in the present invention was obtained by artificial propagation, not wild coral.

First, a coral fragment in the form of a dot was taken from the propagated mother coral, and the coral fragment in the form of a dot comprised a calcium carbonate particle and coral polyps, and the particle diameter of the calcium carbonate particles was about 0.2 cm to 0.5 cm. The coral fragment in the form of a dot was inoculated and fixed on a cylindrical ceramic base plate or a cement plate to facilitate the growth of the coral fragments, and the density of the coral fragments in the form of a dot was 50 to 60 per square meter. During inoculation, the coral fragments in the form of a dot only leaved the seawater shortly. Further, the coral polyps comprised symbiotic algae.

After the inoculation of the coral fragments was completed, rotifers were provided as food and coral feeding was carried out 1 to 3 times a week, and continuous monitoring of the water quality and aquarium water parameters of the circulating seawater was carried out at a frequency of 8 to 12 times a day. Automatic replenishment and a water purification module were set to maintain the circulating seawater had a pH of 7.8 to 8.8, a salinity of 29 ppt to 37 ppt, an alkalinity of 7 dKH to 10 dKH, a temperature of 20° C. to 26° C., a phosphate concentration that was less than 0.03 ppm, a nitrate concentration that was less than 0.1 ppm, a nitrite concentration that was less than 0.1 ppm, a calcium ions concentration of 430 ppm to 500 ppm, and the magnesium ions concentration of 1290 ppm to 1500 ppm.

A water storage tank was set below the glass culturing tank to store filtered clean seawater and was equipped with a water purification module. The water purification module comprised a biochemical cotton with a pore size of 0.1 mm, a biochemical cotton with a pore size of 0.3 mm, a ceramic ring with a pore size of 0.01 mm to 0.05 mm, a filter cotton with a pore size of 0.1 mm to 0.3 mm, coral bone stones and live rock of coral reefs to quickly process and control the water quality of the circulating seawater. Besides, the floating foam on the surface of the circulating seawater was removed by the protein skimmer to reduce the organic substance such as proteins and amino acids, etc. produced by the coral.

The light-emitting diodes (LED) comprising a white LED of 2800K to 3800K, a white LED of 5000K to 6500K, a blue LED of 425 nm to 435 nm, and a blue LED of 445 nm to 470 nm were used. The light was provided at intervals, and the light time was 12 hours in total per day to facilitate the photosynthesis of symbiotic algae. The coral fragments were cultivated and harvested after 550 days to obtain a whole coral with a vertical height of 12 cm to 20 cm and a branch length of 5 cm to 15 cm. The coral polyps were removed and the whole corals were cleaned to obtain the coral bones.

PREPARATION EXAMPLE 2

Porous Tricalcium Phosphate Material

The coral bones of Preparation Example 1 were ground into powders to obtain coral calcium carbonate. The coral calcium carbonate, commercial dicalcium phosphate and sterile water were mixed at a weight ratio of 1:3:6 in a mixing bucket to obtain a first mixture. The sterile water per se served as medium and did not participate in the formation reaction of tricalcium phosphate.

The brushless stirrer was put into the mixing bucket. As both coral calcium carbonate and dicalcium phosphate had a specific weight higher than that of the sterile water and settled to the bottom of the mixing bucket, the head of the stifling rod was set to reach the bottom of the mixing bucket and stirred at a speed of 400 rpm to 500 rpm for 7 hours to 11 hours, and then the stirred first mixture was dried by heat at 50° C. to 60° C. for 7 hours to 10 hours to obtain dried powders.

The dried powders were poured into an alumina crucible which was further placed in the center of a heating furnace and heated at a constant temperature in the general atmosphere, wherein the heating step was divided into two stages: the temperature climbing rate in the first stage was controlled within the range of 5° C. per minute or less and the temperature increased from room temperature to 500° C. to 600° C., and was maintained at 500° C. to 600° C. for 2 hours to 3 hours. The temperature climbing rate in the second stage was controlled within the range of 5° C. per minute or less, and the temperature increased from the final temperature of the first stage to 1000° C. to 1100° C., and was maintained at 1000° C. to 1100° C. for 2 hours to 4 hours. The heating step was then ended, so that the heating furnace could cool down gradually to decrease the temperature of the powders after heat treatment.

The powders after heat treatment were filtered. The filtering method was to place the powders after heat treatment on No. 5B filter paper, and then wash the powders after heat treatment with sterile water to remove water-soluble impurities. The air suction filter was used to accelerate the discharge of the filtrate, and the filtering step stopped until the pH of the filtrate reached 7 to 8 to obtain filtered powders.

The filtered powders were dried by heat at 50° C. to 60° C. for 7 hours to 10 hours, and a multilayer stainless steel screen with each layer thereof having different pore diameters was used for particle size classification to obtain tricalcium phosphate particles within various diameter ranges. The porous tricalcium phosphate material of the present invention with an average particle diameter of 3 millimeters (mm) was chosen for further testing.

Test 1: Compressive Strength

The porous tricalcium phosphate material of the present invention was Example 1(E1), which was the porous tricalcium phosphate material obtained in Preparation Example 2 with an average particle diameter of 3 mm. The tricalcium phosphate of the commercial bone grafting medical device, hereinafter referred to as commercial tricalcium phosphate, was Comparative Example 1(CE1); wherein the product name of commercial tricalcium phosphate is NuROs, Bone Graft Substitute (Sterile), DOH Medical Device Manufacturing No. 003611, REF BGD50, and has an average particle diameter of 3 mm. The ingredient of the commercial tricalcium phosphate was pure tricalcium phosphate (β-TCP). Ten sample powders of each of E1 and CE1 were prepared for testing. This test was carried out according to the Charter of 4.6.2.4 in the regulations of ISO 13175-3(2012), wherein the environmental temperature was 23±2° C., and relative humidity was 50±10%. Both E1 and CE1 were in the form of compressed tablet with a thickness of 5 mm and a diameter of 13 mm, prepared by hydraulic pressure and tested by Criterion C43 Universal Testing Machine (MTS) at the test speed of 0.5 mm/min. The results were shown in Table 1.

TABLE 1

| maximum load (Unit: kgf) | | |
|---|---|---|
| Serial numbers | E1 | CE1 |
| #1 | 7.0 | 1.4 |
| #2 | 5.1 | 5.9 |
| #3 | 7.3 | 1.7 |
| #4 | 5.4 | 1.2 |
| #5 | 6.4 | 2.8 |
| #6 | 7.4 | 1.6 |
| #7 | 6.7 | 1.3 |
| #8 | 5.9 | 5.6 |
| #9 | 9.0 | 3.8 |
| #10 | 2.1 | 0.8 |
| Average | 6.2 | 2.6 |
| S.D. | 1.8 | 1.9 |

According to Table 1, the average maximum load of E1 was 2.38 times of that of CE1 under the same sample preparation method and test conditions. Besides, the max value of the average maximum load of E1 may reach 9.0 kgf, whereas that of CE1 was only 5.9 kgf, which was even lower than the average maximum load of E1, which was 6.2 kgf. Therefore, the average maximum load of the porous tricalcium phosphate material of the present invention was significantly better than that of the commercial tricalcium phosphate and the risk that the accelerated degradation of the substitute bone material resulted from the stress from the patients' body weight could be lowered, which means the present invention was more suitable for bone healing for the patients.

Test 2: Elastic Modulus

E1 and CE1 in Test 2 were the same as those in Test 1, and ten sample powders of each of E1 and CE1 were prepared for testing as well. This test was carried out according to the regulations of ISO 13175-3(2012), wherein the environmental temperature, relative humidity, sample preparation method, the machine and test speed for sample testing were the same as those in Test 1. The results were shown in Table 2.

TABLE 2

| Elastic modulus (Unit: Gpa) | | |
|---|---|---|
| Serial numbers | E1 | CE1 |
| #1 | 0.421 | 0.053 |
| #2 | 0.226 | 0.134 |
| #3 | 0.502 | 0.080 |
| #4 | 0.196 | 0.029 |
| #5 | 0.334 | 0.408 |

TABLE 2-continued

| Elastic modulus (Unit: Gpa) | | |
|---|---|---|
| Serial numbers | E1 | CE1 |
| #6 | 0.332 | 0.055 |
| #7 | 0.225 | 0.056 |
| #8 | 0.267 | 0.278 |
| #9 | 0.646 | 0.105 |
| #10 | 0.069 | 0.020 |
| Average | 0.322 | 0.122 |
| S.D. | 0.166 | 0.125 |

According to Table 2, the average elastic modulus of E1 was 2.64 times of that of CE1 under the same sample preparation method and test conditions. Therefore, the average elastic modulus of the porous tricalcium phosphate material of the present invention was significantly better than that of the commercial tricalcium phosphate and the cracking risk could be lowered, which means the present invention was more suitable for bone healing for the patients.

Test 3: Water Solubility

E1 and CE1 in Test 3 were the same as those in Test 1. This test was carried out according to the regulations of ISO 13175-3(2012), wherein 100 mL of water was added with E1 and CE1, respectively and stirred at 20° C. until E1 and CE1 no longer dissolved in the water. The results were shown in Table 3.

TABLE 3

| Water solubility (20° C.) | | |
|---|---|---|
| Item | E1 | CE1 |
| Solubility | 0.0038 g/100 mL | 0.0040 g/100 mL |

According to Table 3, the water solubility of E1 and CE1 was similar, and that of E1 was slightly lower than that of CE1. As both the porous tricalcium phosphate material of the present invention and the commercial tricalcium phosphate were hardly dissolved in water so as to avoid the risk of instant dissolution after implantation into human body, that means both of the two were suitable for bone healing for the patients.

Test 4: Pore Analysis

Figure 2:
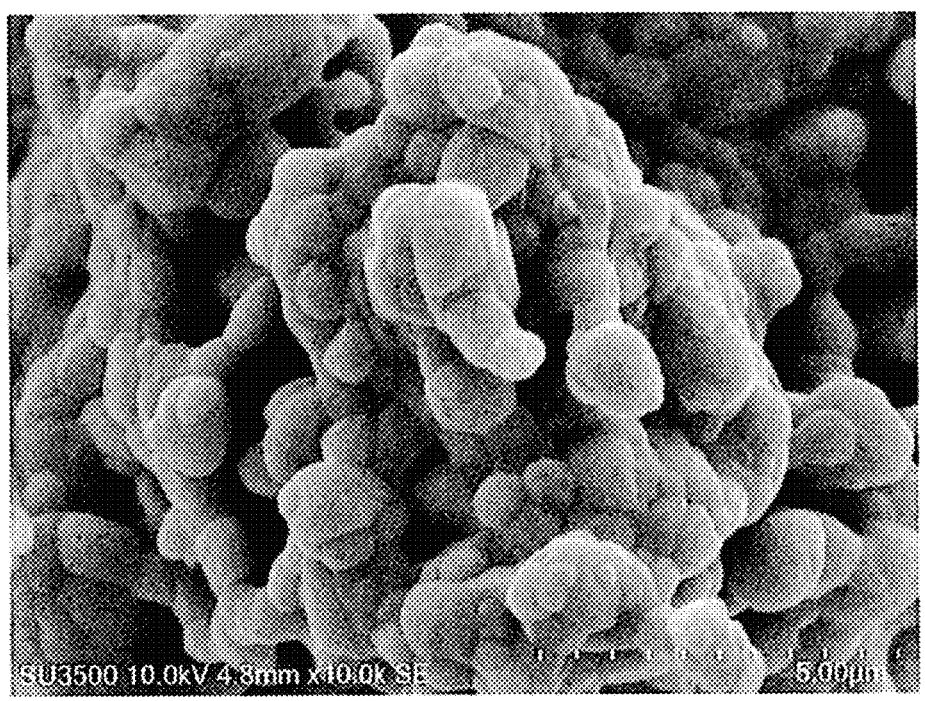
FIG. 2 is the magnified photo of the porous tricalcium phosphate material of Comparative Example 1 of the commercial product.

E1 and CE1 in Test 4 were the same as those in Test 1, wherein the magnified photo of E1 was shown in FIG. 1 and the pore 1 was marked. The magnified photo of CE1 was shown in FIG. 2. This test was carried out according to the Charter of 4.4.2.1 in the regulations of ISO 13175-3(2012). Mercury Porosimeter and Scanning Electron Microscope (SEM, HITACHI SU3500) were used for testing. The results were shown in Table 4, wherein the calculation formula of the total porosity is $\varepsilon p = Vt\, \rho s/(Vt\, \rho s+1)*100\%$.

TABLE 4

| Total pore volume, density, average pore size and total porosity | | |
|---|---|---|
| Item | E1 | CE1 |
| Total pore volume (Vt) | 0.4361 mL/g | 0.5233 mL/g |
| Density (ρs) | 1.8745 g/mL | 1.7632 g/mL |
| Average pore size | 1.35527 μm | 1.44785 μm |
| Total porosity (εp) | 44.9784% | 47.9873% |

According to Table 4, the total pore volume of the tricalcium phosphate of E1 per gram is 0.4361 mL/g, the average pore size (diameter) was 1.35527 μm and the total porosity was 44.9784%, which indicated that E1 indeed was porous materials.

In contrast, first, the total pore volume of the tricalcium phosphate of E1 per gram was about 83% of that of CE1, wherein 83% was obtained by the calculation formula of (0.4361/0.5233)*100. Second, the total porosity of E1 was about 93.7% of that of CE1. Third, the average pore size (diameter) of E1 was about 93.6% of that of CE1. Fourth, the density of E1 was about 106.3% of that of CE1. Therefore, the differences among the measurement results of the pore and density of E1 and CE1 were 6% to 17%, which indicated that the pore structure of the claimed porous material was different from that of the commercial tricalcium phosphate, and such differences may result from a different raw material, coral bones, adopted in the present invention.

Test 5: Ca/P Ratio

Figure 3:
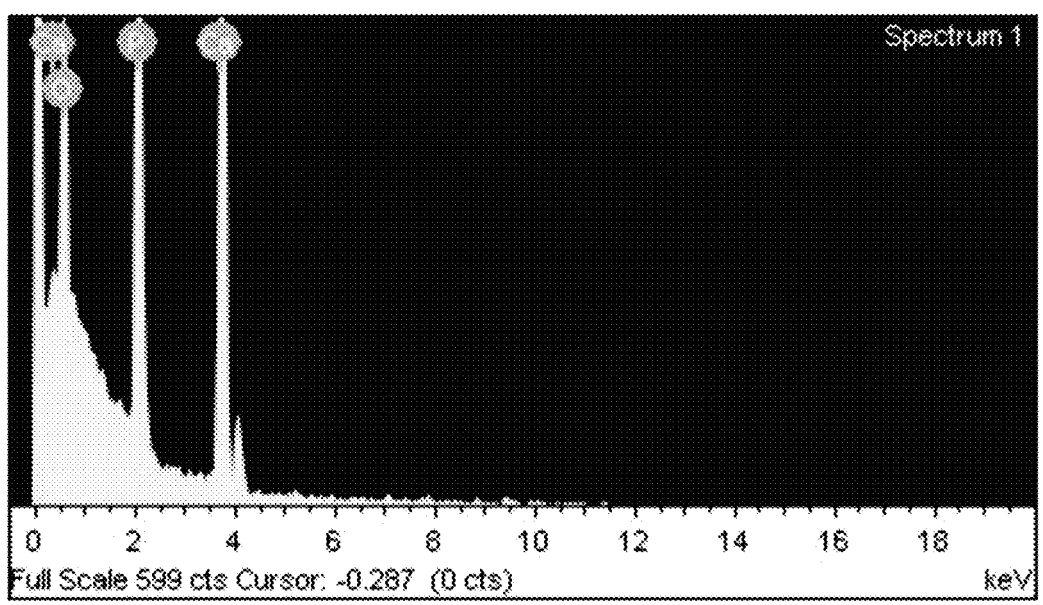
FIG. 3 is an Energy Dispersive Spectrum (EDS) result graph of the porous tricalcium phosphate material of Example 1 of the present invention.

This test was carried out according to the regulations of ISO 13175-3(2012) for E1 and Scanning Electron Microscope and Energy Dispersive Spectrometer (S3400N) was used for testing. The results were shown in Table 5 and FIG. 3.

TABLE 5

| | Ca/P ratio | |
|---|---|---|
| Item | Weight percentage (%) | Atomic percentage (%) |
| Oxygen (O) | 50.70 | 69.78 |
| Phosphorus (P) | 19.34 | 13.75 |
| Calcium (Ca) | 29.96 | 16.46 |

According to Table 5, the weight ratio of calcium to phosphorus of the porous tricalcium phosphate material of the present invention was 29.96/19.34=1.55.

Test 6: Heavy Metals Test

This test was carried out according to the regulations of ISO 13175-3(2012) for E1 and Inductively coupled plasma-optical emission spectrometry (ICP-OES) was used for testing. The results were shown in Table 6.

TABLE 6

| | Heavy metals test | |
|---|---|---|
| Item | Test result (ppm) | Limit of quantitation (ppm) |
| Lead (Pb) | Not-detected | 1.0 |
| Cadmium (Cd) | Not-detected | 1.0 |
| Mercury (Hg) | Not-detected | 1.0 |
| Arsenic (As) | Not-detected | 1.0 |

According to Table 6, lead, cadmium, mercury and arsenic were not-detected in E1, which indicated that the porous tricalcium phosphate material of the present invention was free of heavy metals and will not cause negative effect on the body of the patients and was beneficial for the patients.

Test 7: Fourier Transform Infrared Spectroscopy Analysis

E1 and CE1 in Test 7 were the same as those in Test 1. This test was carried out according to the regulations of ISO 13175-3(2012) and Fourier transform infrared spectroscopy (FTIR) was used for testing. The measurement results of E1 and CE1 were shown in FIGS. 4A and 4B.

Figure 4A:
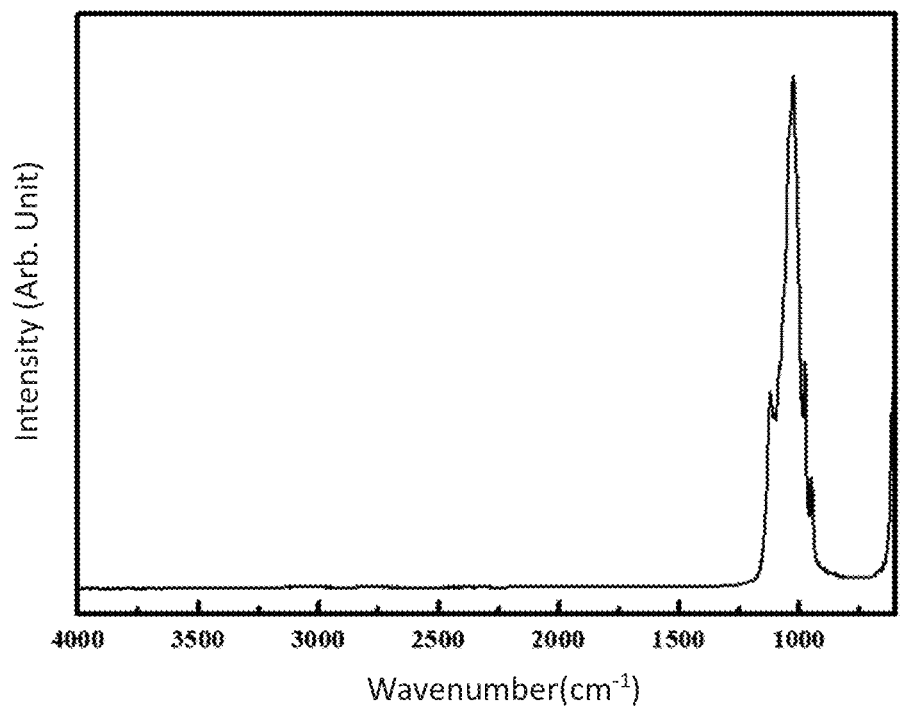
FIGS. 4A and 4B are the respective Fourier-transform infrared spectroscopy (FTIR) spectrogram results of Example 1 and Comparative Example 1 of the commercial product, respectively.
Figure 4B:
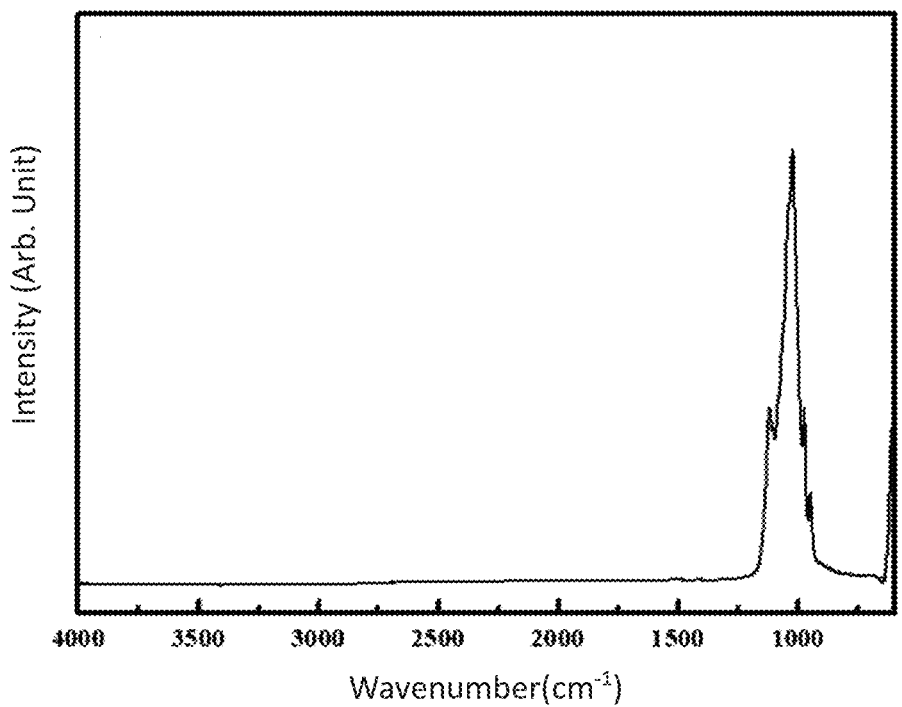

According to the comparison of FIGS. 4A and 4B, the spectrum analysis results of E1 and CE1 were similar, and the major ingredient was calcium phosphate salt, which was pure tricalcium phosphate. Besides, the package insert of CE1 disclosed that the ingredient was pure tricalcium phosphate (β-TCP). Therefore, the porous tricalcium phosphate material of the present invention was also pure tricalcium phosphate (β-TCP), and could be used for bone healing as well.

Test 8: Bone Healing Efficacy Test

The bone healing efficacy test was carried out according to Biological evaluation of medical devices—Part 6: Tests for local effects after implantation ISO 10993 (2016)). The experimental animal was male New Zealand White rabbit, which had a body weight ≥2.8 kg and an age ≥8 months at the time of surgery to ensure skeletal maturity thereof. During this test, one rabbit was raised in one cage, the temperature of the environment was 19±3° C. with the humidity of 50±20%, and the light cycle was 12 hours light and 12 hours dark. The name of the feed was Prolab Rabbit Diet, purchased from PMI Nutrition International (U.S.A.), and the way to supply the feed was ad libitum. The drinking water was RO water, and the way to supply was ad libitum as well.

E1 and CE1 in Test 8 were the same as those in Test 1. Prior to this test, the fur of experimental animal's thigh was clipped with an electric shaver, and Zoletil and xylazine were injected into the muscle of the rabbits at the dose of 10 mg/kg separately for anesthesia, and the anesthesia was maintained by providing isoflurane during the surgery. The surgery was provided to create a defect of 6 mm diameter and 10 mm depth in the heads of distal femoral of both left and right thighs of the experimental animals with a drill, and then the powders of E1 were compressed into the defects in the right thigh as an implant, and the powders of CE1 were compressed into the defects in the left thigh as an implant. After surgery, antibiotics were administered once per day for seven days.

The experimental animals implanted with both E1 and CE1 were divided into three groups and sacrificed after raising for 4 weeks (W4 group), 12 weeks (W12 group) and 26 weeks (W26 group). There are 8 rabbits for each group and 24 rabbits in total. During the test period, body weights, any abnormal behavior and wound conditions of the experimental animals were observed.

After the experimental animals were sacrificed, the tissues surrounding the implant sites were examined for gross finding which included haematoma, oedema and encapsulation.

Figure 5A:
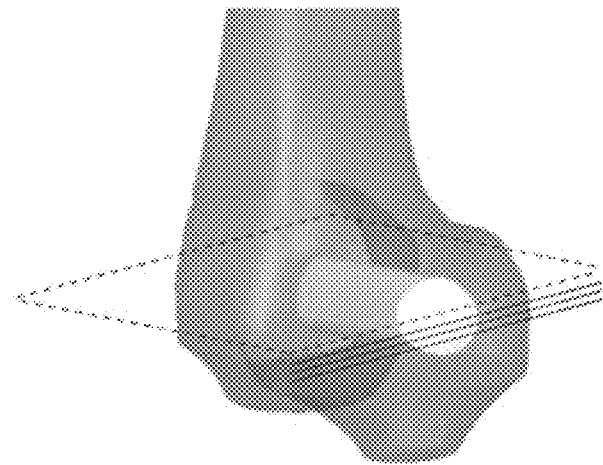
FIGS. 5A and 5B are the schematic diagrams of the distal femora to show slice direction and the obtained bone section, respectively.
Figure 5B:
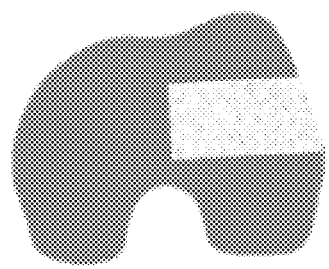

After the surrounding tissues were removed, section preparation and staining were carried out for the distal femoral of both left and right thighs, and the steps were as follows: After the adjacent muscle and soft tissues were carefully removed to obtain the specimens, the specimens were fixed in 10% buffered neutral formalin solution for 24 hours and then dehydrated in ethanol and embedded in methyl methacrylate. After polymerization, a diamond blade-equipped microtome was used for sectioning the embedded specimens in a transversal direction (as shown in FIG. 5A) to obtain non-decalcified thin sections (~500 μm) (as shown in FIG. 5B), which was further stained with Masson's trichrome stain to obtain bone sections. Finally, the respective area proportion of the new bone formation, residual bone substitute and void space of the bone sections were analyzed and quantified by the software of Media Cybernetics Imagine Pro Plus (IPP) program, and the comparison results of E1 and CE1 were obtained by One-way ANOVA test of JMP statistical software and the Student's t-test (1) Body Weights, any Abnormal Behavior and Wound Conditions of the Experimental Animals In W4 group, the body weight of the experimental animals increased from the range of 2730 g to 2833 g after surgery to the range of 2862 g to 3101 g. In W12 group, the body weight of the experimental animals increased from the range of 2705 g to 2841 g after surgery to the range of 3965 g to 4103 g. In W26 group, the body weight of the experimental animals increased from the range of 2681 g to 2811 g after surgery to the range of 4031 g to 4120 g. Therefore, the body weight of the experimental animals in each group increased steadily or normally. Besides, no abnormal behaviors and wound infections were found during the test period, so the wound healed well. In other words, the health status of the experimental animals were healthy and showed no immunological rejection response.

(2) Observation of any Haematoma, Oedema and Encapsulation of Experimental Animals In W4, W12 and W26 groups, no haematoma, oedema and encapsulation in the tissues surrounding the implant sites was observed in all experimental animals implanted with E1 and CE1. Therefore, all experimental animals implanted with E1 and CE1 healed well.

(3) The Respective Area Proportion of the New Bone Formation, Residual Bone Substitute and Void Space of the Bone Sections The statistical data of the histomorphometry of the bone sections were shown in Table 7, wherein a total of 100% was obtained after adding up the respective area proportion of the new bone formation, residual bone substitute and void space of the bone sections.

TABLE 7 the respective area proportion of the new bone formation, residual bone substitute and void space of the bone sections

| Group | Implanted Item | New bone formation (%) | Residual bone substitute (%) | Void space (%) |
|---|---|---|---|---|
| 4 Weeks (W 4) | E1 | 6.31 ± 2.71 | 60.18 ± 17.51 | 33.51 ± 16.47 |
| | CE1 | 12.56 ± 4.29 | 25.05 ± 4.40 | 62.39 ± 3.39 |
| | p value | 0.004 | 0.00007 | 0.00019 |
| 12 Weeks (W 12) | E1 | 17.21 ± 7.96 | 37.69 ± 5.14 | 45.10 ± 9.40 |
| | CE1 | 17.43 ± 8.45 | 15.39 ± 7.68 | 67.18 ± 8.57 |
| | p value | 0.96 | 0.00001 | 0.00004 |
| 26 Weeks (W 26) | E1 | 19.46 ± 3.99 | 22.06 ± 14.73 | 58.48 ± 14.13 |
| | CE1 | 11.71 ± 4.73 | 2.65 ± 2.22 | 85.64 ± 4.05 |
| | p value | 0.003 | 0.002 | 0.00068 |

In W4 group, the area proportion of the new bone formation of CE1 was 12.56%, which was about double of that of E1 (6.31%) and a statistically significant difference was found. However, in W26 group, the area proportion of the new bone formation of CE1 was 11.71%, which was about half of that of E1 (19.46%) and a statistically significant difference was found. Hence, CE1 provided better short-term bone healing efficacy, and E1 provided significantly better long-term bone healing efficacy.

Second, according to the change of the area proportion of the new bone formation in W4, W12 and W26 groups, the area proportion of the new bone formation of E1 increased continually from 6.31% to 19.46%, but that of CE1 reduced from 12.56% to 11.71%. As bone healing generally requires a long period, the porous tricalcium phosphate material of the present invention is more suitable for bone healing of the patients.

Third, according to the area proportion of the new bone formation and residual bone substitute in W26 group, the area proportion of the residual bone substitute of CE1 was only 2.65%, it was believed that the implant of CE1 probably degraded too fast in vivo to provide support for the new bone formation and resulted in that the growing rate of new bone was slower than the degradation rate of new bone. In comparison, the porous tricalcium phosphate material of the present invention has a degradation rate that not only was slower than that of CE1 but also gradually slowed down during the test period to provide a longer period for new bone adhesion, and is more suitable for bone healing of the patients.

Figures 6A, 6B, 6C:
FIG. 6A to FIG. 6C are the bone section photos of the representative Week 4 (W4) group of Example 1.
Figures 6D, 6E, 6F:
FIG. 6D to FIG. 6F are the bone section photos of the representative W4 group of Comparative Example 1.
Figures 6G, 6H, 6I:
FIG. 6G to FIG. 6I are the bone section photos of the representative Week 12 (W12) group of Example 1.
Figures 6J, 6K, 6L:
FIG. 6J to FIG. 6L are the bone section photos of the representative W12 group of Comparative Example 1
Figures 6M, 6N, 6O:
FIG. 6M to FIG. 6O are the bone section photos of the representative Week 26 (W26) group of Example 1.
Figures 6P, 6Q, 6R:
FIG. 6P to FIG. 6R are the bone section photos of the representative W26 group of Comparative Example 1.

Finally, as mentioned above, there were 24 experimental animals in this test, and the powders of E1 were compressed into the defects in the right thigh as an implant, and the powders of CE1 were compressed into the defects in the left thigh as an implant, so there were 48 data in total. Due to the large amount of data, the data close to that listed in Table 7 were chosen as the representative groups and shown in Table 8, and FIGS. 6A to 6R were the photos of bone sections of the corresponding representative groups, wherein the gray area indicated said new bone formation, the black area indicated said residual bone substitute, and the white area indicted said void space. Due to the grayscale photo hardly differentiated different areas, the area proportion data shown in Table 8 was used for the following demonstration.

TABLE 8 the representative groups of E1 and CE1 in W 4, W 12 and W 26 groups and the respective area proportion of the new bone formation, residual bone substitute and void space of the bone sections thereof

| Group | Implanted Item | New bone formation (%) | Residual bone substitute (%) | Void space (%) | Figures |
|---|---|---|---|---|---|
| W 4 | E1 | 7.1 | 65.0 | 27.9 | 6A, 6B, 6C |
| | CE1 | 14.2 | 25.8 | 60 | 6D, 6E, 6F |
| W 12 | E1 | 19.4 | 36.1 | 44.5 | 6G, 6H, 6I |
| | CE1 | 13.7 | 20.9 | 65.4 | 6J, 6K, 6L |
| W 26 | E1 | 19.0 | 16.3 | 64.7 | 6M, 6N, 6O |
| | CE1 | 12.1 | 0.5 | 87.4 | 6P, 6Q, 6R |

According to Table 8, the area proportion of the residual bone substitute (black area) of the representative groups of E1 decreased gradually as the weeks of the test period increased, and decreased from 65.0% in W4 group to 16.3% in W26 group. On the other hand, the area proportion of new bone formation (gray area) of the representative groups of E1 increased gradually as the weeks of the test period increased, and increased from 7.1% in W4 group to 19.0% in W26 group, which indicated that the present invention indeed continuously increased the area proportion of new bone formation to heal bones. In contrast, the area proportion of new bone formation of the representative groups of CE1 in W4 and W26 groups were similar, which means there was no significant change of the gray area proportion, and the respective area proportions of new bone formation (gray area) in W4, W12 and W26 groups were 14.2%, 13.7% and 12.1%, which showed that the area proportion of the new bone formation continuously decreased. Therefore, the present invention provided bone healing efficacy.

Test 9: Phase Purity Analysis

The phase purity of E1 was examined according to the regulations of the Charter of 4.2 in ISO 13175-3(2012), and the equipment of D8 DISCOVER SSS Multi Function High Power X-ray Diffractometer was used and the angle range was 2θ from 20° to 80°.

The test result of the phase purity is that the crystallinity is 80.2%, and the amorphous is 19.8%. Therefore, the tricalcium phosphate comprised a high proportion of crystals.

To sum up, the porous tricalcium phosphate material of the present invention not only has the advantages of biocompatibility and no occurrence of immunological rejection response, but also has a significantly better average compressive strength, average elastic modulus and bone healing efficacy, which better meets the needs of the patients.

What is claimed is:

1. A porous tricalcium phosphate material, modified from a coral bone and having a plurality of pores, wherein
   the porous tricalcium phosphate material is β-tricalcium phosphate,
   the weight ratio of calcium to phosphorus of the porous tricalcium phosphate material is 1.5 to 1.6,
   the average total pore volume of the porous tricalcium phosphate material is 0.35 mL/g to 0.51 mL/g,
   the average pore size of the porous tricalcium phosphate material is 1.3 μm to 1.4 μm,
   the average elastic modulus of the porous tricalcium phosphate material is 0.19 Gpa to 0.65 Gpa,
   the density of the porous tricalcium phosphate material is 1.8 g/mL to 2 g/mL,
   the crystallinity of the porous tricalcium phosphate material is 79.4% to 81% and the amorphous thereof is 19% to 20.6%, and
   according to ISO 13175-3(2012), when the porous tricalcium phosphate material is in the form of a circular cylinder with a diameter of 13 mm, the average maximum load of the porous tricalcium phosphate material is 4 kilogram-force (kgf) to 9 kgf.

2. The porous tricalcium phosphate material as claimed in claim 1, wherein the coral bone is obtained from a coral comprising a small polyp stony coral.

3. The porous tricalcium phosphate material as claimed in claim 2, wherein the small polyp stony coral is selected from the group consisting of *Acropora formosa, Acropora nobilis, Acropora austere, Acropora valenciennesi, Acropora pulchra, Acropora microphtha, Acropora intermedia* and *Acropora florida*.

4. A method for bone healing, comprising administering to a subject in need thereof a medical product, wherein the medical product comprises the porous tricalcium phosphate material as claimed in claim 1.

5. The method as claimed in claim 4, wherein the bone healing comprises increasing the growth rate of new bone or increasing the space for bone cell adhesion.

6. A method for bone healing, comprising administering to a subject in need thereof a medical product, wherein the medical product comprises the porous tricalcium phosphate material as claimed in claim 2.

7. The method as claimed in claim 6, wherein the bone healing comprises increasing the growth rate of new bone or increasing the space for bone cell adhesion.

* * * * *